United States Patent

Okada et al.

Patent Number: 5,191,117
Date of Patent: Mar. 2, 1993

[54] SULFONAMIDE DERIVATIVE

[75] Inventors: Hisashi Okada; Morio Yagihara, both of Kanagawa, Japan

[73] Assignee: Fuji Photo Film Co., Ltd., Kanagawa, Japan

[21] Appl. No.: 812,938

[22] Filed: Dec. 24, 1991

[30] Foreign Application Priority Data

Dec. 25, 1990 [JP] Japan .................. 2-405649

[51] Int. Cl.$^5$ .................. C07C 315/00; C07C 303/00
[52] U.S. Cl. .................. 562/556; 560/250; 560/252; 564/80; 564/82
[58] Field of Search .................. 562/556; 560/250, 252

[56] References Cited

FOREIGN PATENT DOCUMENTS

| | | | |
|---|---|---|---|
| 291482 | 9/1953 | Fed. Rep. of Germany | 562/556 |
| 327717 | 6/1954 | Fed. Rep. of Germany | 562/556 |
| 333011 | 11/1958 | Fed. Rep. of Germany | 562/556 |
| 3324236 | 1/1985 | Fed. Rep. of Germany | 562/556 |
| 61-100266 | 5/1986 | Japan | |

OTHER PUBLICATIONS

Murase et al., "Bis(isocyclam)dicopper(II) complexes w/ a linear methylene chain bridge", *Inorg. Chim. Acta*, 11/(1), 57-60, Chem. Abstract only CA 104(20):179019d, (1986).

Translation of claims of Japanese Patent Laid-Open Publication No. 61-100266 May 19, 1986.

*Primary Examiner*—Jose' G. Dees
*Assistant Examiner*—Keith MacMillan
*Attorney, Agent, or Firm*—Sughrue, Mion, Zinn, Macpeak & Seas

[57] ABSTRACT

The sulfonamide derivative according to the present invention is expressed by a general formula:

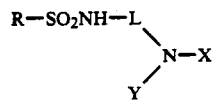

(where R represents an alkyl group. —X represents —$L_{12}$—COOM or

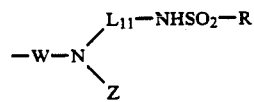

and Y— represents R—$SO_2$NH—$L_{11}$— or MOO-C—$L_{12}$—. Each of $L_{11}$ and $L_{12}$ represents an alkylene group. Z is identical to Y, and M represents a hydrogen atom or a cation. However, X and Y cannot be —$L_{12}$—COOM at the same time. W represents an alkylene group or a cycloalkylene group having 2 or more carbon atoms.)

This compound is useful as a metallic ion shielding agent and is suitable, for example, for the applications such as photographic processing solution, chelate titration or analytical reagent for medical treatment or for medical drugs as a metallic ion shielding agent.

12 Claims, No Drawings

SULFONAMIDE DERIVATIVE

BACKGROUND OF THE INVENTION

The present invention relates to a new sulfonamide derivative useful as a metallic ion shielding agent.

As a compound of this type, there has been known a sulfonamide derivative given by the following general formula:

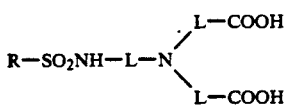

(where R represents an alkyl group or an aromatic group having 6 or more carbon atoms, and L represents an alkylene group.), or a sulfonamide derivative given by the following general formula:

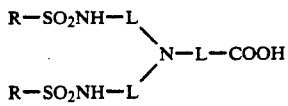

(where R represents an aromatic group, and L an alkylene group.), whereas none of these compounds is known as a metallic ion shielding agent.

When it is attempted to use the compound as a metallic ion shielding agent, solubility to water is low, and deposition occurs when the compound is used or it is used as a chelate of metal. This causes problems, for example, when the compound is used as a metallic ion shielding agent for photographic processing solution, for chelate titration or for analytical reagents for medical treatment or for medical drugs.

It is an object of the present invention to provide a new sulfonamide derivative useful as a metallic ion shielding agent.

SUMMARY OF THE INVENTION

The sulfonamide derivative according to the present invention is characterized in that it is expressed by the following formula (A):

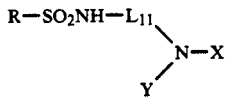

(where R represents an alkyl group. —X represents —$L_{12}$—COOM or

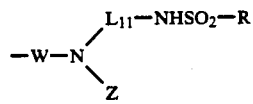

and Y— represents R—$SO_2$NH-$L_{11}$— or MOOC—$L_{12}$—. Each of $L_{11}$ and $L_{12}$ represents an alkylene group. Z is identical to Y, and M represents a hydrogen atom or a cation. However, X and Y cannot be —$L_{12}$-COOM at the same time. W represents an alkylene group having 2 or more carbon atoms.)

The solfonamide derivative according to the present invention is soluble in water and is suitable for the applications such as photographic processing solution, chelate titration or analytical reagent for medical treatment or for medical drugs as a metallic ion shielding agent.

The above and other objects, features and advantages of the present invention will become apparent from the following description, in which preferred embodiments of the present invention are shown by way of illustrative examples.

DESCRIPTION OF THE PREFERRED EMBODIMENTS

Among the sulfonamide derivative given by the general formula (A), the sulfonamide derivatives given by the following general formulae (B), (C) and (D) are particularly useful.

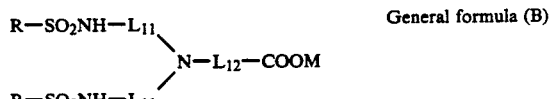

General formula (B)

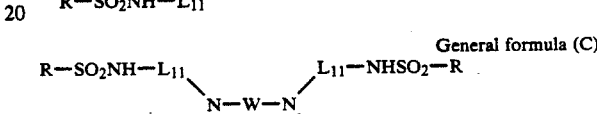

General formula (C)

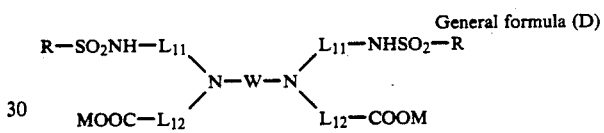

General formula (D)

In the following, detailed description is given on the preferred sulfonamide derivatives of the present invention.

In a sulfonamide derivative given by each of the above general formulae, the alkyl group expressed by R may be in form of a straight chain, a branched chain or a ring. The number of carbon atoms is 1 to 10, or preferably, 1 to 5, or more preferably, 1. As the alkyl group, there are, for example, methyl group, ethyl group, n-propyl group, i-propyl group, n-butyl group, i-butyl group, t-butyl group, n-pentyl group, i-pentyl group, t-pentyl group, cyclopentyl group, n-hexyl group, cyclohexyl group, 2-ethylhexyl group, etc.

R may be provided with a substituent. As the substituent, there are, for example, alkoxy group, amino group, acylamino group, sulfonylamino group, ureide group, urethane group, aryloxy group, sulfamoyl group, carbamoyl group, alkylthio group, arylthio group, sulfonyl group, sulfinyl group, hydroxy group, halogen atom, cyano group, sulfo group, carboxyl group, phosphono group, aryloxycarbonyl group, acyl group, alkoxycarbonyl group, acyloxy group, carbonamide group, sulfonamide group, nitro group, hydroxamic acid group, etc. Preferably, it is a halogen atom. Particularly, a fluorine atom is useful.

As an alkyl group represented by R, the most preferable is a methyl group.

The alkylene group given by $L_{11}$ and $L_{12}$ may contain a substituent. As such substituent, the substituent given for R may be used.

$L_{11}$ and $L_{12}$ may be in form of a straight chain, a branched chain or a ring. The number of carbon atoms is preferably 1 to 3. For example, methylene group, ethylene group, trimethylene group, propylene group, etc. may be used. In particular, methylene group and ethylene group are preferable.

As a cation given by M, there are alkali metal (such as Li, Na, K), ammonium (such as ammonium, triethyl ammonium).

The alkylene group and the cycloalkylene group represented by W may have a substituent. As such substituent, the substituent given for R can be cited.

The alkylene group represented by W has 2 or more carbon atoms, preferably 2 to 5 carbon atoms, or more preferably, 2 to 3. It may be in form of a straight chain, or a branched chain. Particularly, a propylene group is preferable.

The cycloalkylene group represented by W has 3 or more carbon atoms, preferably 3 to 10 carbon atoms, or more preferably, 4 to 6. Particularly, a cyclohexylene group is preferable.

As concrete examples of W, the following may be used:

—(CH$_2$)$_2$—, —(CH$_2$)$_3$—, —(CH$_2$)$_4$—, —CH(CH$_3$)CH$_2$—,

—CH(CH$_3$)CH(CH$_3$)—, —CH$_2$CH(OH)CH$_2$—,

In the following, concrete examples of the sulfonamide derivative (compounds 1 to 10) of the present invention are shown, while it is not limited to these examples.

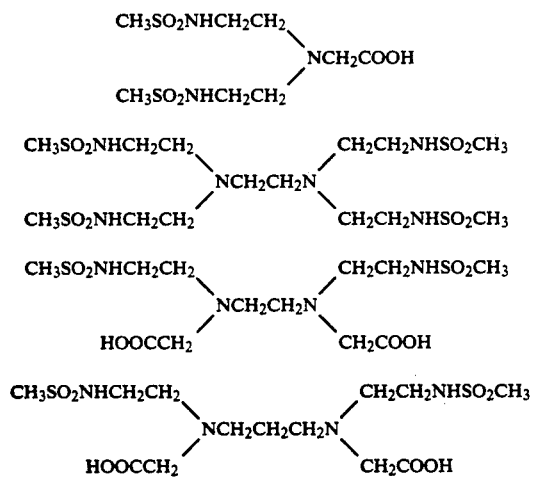

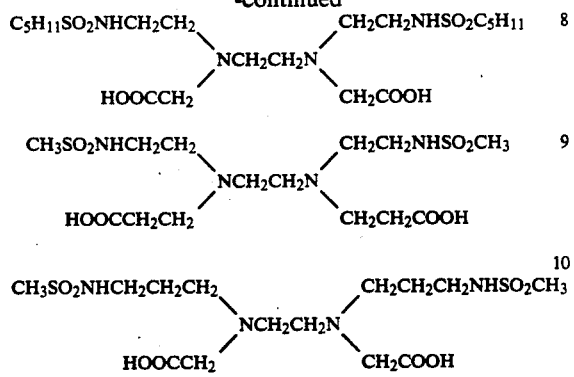

The sulfonamide derivative given by the above general formula (A) can be synthesized, for example, by the following method:

Specifically, the compound can be synthesized by reacting a sulfonamide substituent with an alkane with leaving group (e.g. 2-chloroethylmethane sulfonamide, 2-chloroethylpentane sulfonamide, 3-chloropropylmethane sulfonamide, etc.) with amine compound (e.g. N,N'-diacetic acid ethylenediamine, N,N'-diacetic acid propanediamine, ethylenediamine, 1,3-propanediamine, 1,2-cyclohexanediamine, glycine, N,N'-dipropionic acid ethylenediamine, etc.) under the presence of a base.

Also, the compound can be synthesized by reacting a sulfonamide substituent with an alkane having carbonyl group (e.g. 2-methane sulfonamide ethanol, 3-methane sulfonamide propanal, 2-trifluoromethane sulfonamide ethanal, etc.) with amine compound (e.g. the amine compounds as described above) through hydrogenation reaction.

The above reaction according to the present invention is usually performed in a solvent. There is no restriction of the solvent except that it is not related to the reaction. It is preferable to use water, alcohol (lower alcohol such as methanol) to facilitate the reaction.

As an alkane having leaving group, compounds used for alkylation of amino group, such as halogen atom (e.g. chlorine, bromine, iodine, etc.), p-toluene sulfonate group, etc. can be used. As the base to be used, there are alkali or tertiary amine (such as triethylamine).

The base is used by a ratio of equimol - 10 mols to the alkane, or more preferably, equimol - 4 mols. When it is synthesized through hydrogenation reaction, palladium, platinum, cobalt, etc. carried by activated carbon or Raney nickel may be used as a catazlyst.

Reaction temperature is 0° to 100° C., or more preferably, 10° C. to 70° C.

EXAMPLE 1

Synthesis of the compound 1

15.0 g (0.20 mol) of glycine was dissolved in 40 ml (0.20 mol) of 5N sodium hydroxide. While stirring up the solution at 50° C., 66.2 g (0.42 mol) of 2-chloroethylmethane sulfonamide and 84 ml (0.42 mol) of 5N sodium hydroxide were gently dropped so that pH value of the reaction solution was maintained at 10 to 11.

After the dropping was completed, the solution was further stirred up for 5 hours at 50° C. and was cooled down to room temperature, and 20.3 g (0.20 mol) of concentrated hydrochloric acid was added. The deposited solid was collected through filtration and was recrystallized with water. The resultant white solid was dried under reduced pressure, and 20.6 g (0.0649 mol) of the desired compound 1 was obtained.

Yield: 32%. Melting point: 176° to 177° C. (decomposed).

| The results of element analysis | | | | |
|---|---|---|---|---|
| | H | C | N | S |
| Calculated value (%): | 6.03 | 30.28 | 13.24 | 20.21 |
| Measured value (%): | 6.00 | 30.17 | 13.32 | 20.29 |

$^1$HNMR ($D_2O$) δppm,
δ3.13 (s 6H),
δ3.54 (t 4H),
δ3.58 (t 4H),
δ3.90 (s 2H).

EXAMPLE 2

Synthesis of the compound 2

6.0 g (0.10 mol) of ethylenediamine was dissolved in 20 ml of water. While stirring this at 50° C., 66.2 g (0.420 mol) of 2-chloroethylmethane sulfonamide and 84.0 ml (0.420 mol) of 5N sodium hydroxide were gently dropped so that pH value of the reaction solution was maintained at 10 to 11.

After the dropping was completed, it was stirred up for 5 hours at 50° C. and was cooled down to room temperature and was left to stand overnight. The deposited solid was collected through filtration and was recrystallized with water. The resultant white solid was dried under reduced pressure, and 22.2 g (0.0408 mol) of the desired compound 2 was obtained.

Yield: 41%. Melting point: 120° to 121° C.

| The results of element analysis | | | | |
|---|---|---|---|---|
| | H | C | N | S |
| Calculated value (%): | 6.66 | 30.87 | 15.43 | 23.54 |
| Measured value (%): | 6.59 | 30.73 | 15.36 | 23.76 |

$^1$HNMR ($D_2O$) δppm;
δ2.73 (s 4H);
δ2.75 (t 8H);
δ3.08 (s 12H);
δ3.23 (t 8H).

EXAMPLE 3

Synthesis of the compound 3

36.5 g (0.207 mol) of N,N'-diacetic acid ethylenediamine was dissolved in 82.8 ml (0.414 mol) of 5N sodium hydroxide. While stirring it at 50° C., 71.7 g (0.455 mol) of 2-chloroethylmethane sulfonamide and 91.0 ml (0.455 mol) of 5N sodium hydroxide were gently dropped so that pH value of the reaction solution was maintained at 10 to 11.

After the dropping was completed, the solution was stirred up for 3 hours at 50° C. and was cooled down to room temperature. 46.1 g (0.455 mol) of concentrated hydrochloric acid was added, and the solution was condensed under reduced pressure until the volume was reduced to about 50 ml. The deposited sodium chloride was collected through filtration. 46.1 g (0.455 mol) of concentrated hydrochloric acid was added to the filtrate and was condensed again under reduced pressure until the volume of the solution was reduced to about 50 ml, and the resultant sodium chloride was collected through filtration. After performing the same procedure by two more times, methanol was added, and the deposited solid was collected through filtration. By drying this under reduced pressure, 23.1 g (0.0462 mol) of ½ hydrate dihydrochloride of the desired compound 3 was obtained.

Yield: 22%. Melting point: 189° to 190° C. (decomposed).

| The results of element analysis As $C_{12}H_{26}N_4O_8S_2 \cdot 2HCl \cdot \frac{1}{2}H_2O$ | | | | | |
|---|---|---|---|---|---|
| | H | C | N | S | Cl |
| Calculated value (%): | 5.84 | 28.80 | 11.20 | 12.81 | 14.17 |
| Measured value (%): | 5.74 | 28.57 | 11.00 | 12.78 | 14.31 |

$^1$HNMR (D20) δppm,
δ3.13 (s 6H),
δ3.47 (t 4H),
δ3.55 (t 4H),
δ3.68 s 4H),
δ4.08 s 4H).

EXAMPLE 4

Synthesis of the compound 4

14.6 g (0.055 mol) of N,N'-diacetic acid -1,3-propaneamine dihydrochloride was dissolved in 44.4 ml (0.222 mol) of 5N sodium hydroxide. While stirring this at 50° C., 19.3 g (0.123 mol) of 2-chloroethylmethane sulfonamide and 24.6 ml (0.123 mol) of 5N sodium hydroxide were gently dropped so that pH value of the reaction solution was maintained at 10 to 11.

After the dropping was completed, the solution was stirred up for 3 hours at 50° C. and was cooled down to room temperature, and 90.0 g (0.889 mol) of concentrated hydrochloric acid was added. After condensing the reaction solution under reduced pressure until the volume was reduced to about 50 ml, pH was adjusted to about 6 by potassium carbonate and the solution was left overnight. The deposited solid was collected through filtration and was recrystallized with water. By drying the resultant white solid, 4.0 g ($8.54 \times 10^{-3}$ mol) of 2-hydrate of the desired compound 4 was obtained.

Yield: 15%. Melting point: 189° to 190° C. (decomposed).

| The results of element analysis As $C_{13}H_{28}N_4O_8S_2 \cdot 2H_2O$ | | | | |
|---|---|---|---|---|
| | H | C | N | S |
| Calculated value (%): | 6.88 | 33.32 | 11.96 | 13.69 |
| Measured value (%): | 6.81 | 32.50 | 11.78 | 13.65 |

$^1$HNMR (D20) δppm,
δ61.56-1.75 (m 2H),
δ2.58 (t 4H),
δ2.69 (t 2H),
δ2.75 (s 6H),
δ3.01 (t 2H),
δ3.18 (s 4H).

What we claim is:

1. A sulfonamide derivative expressed by the general formula (D):

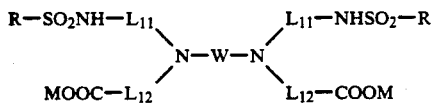

where R represents an unsubstituted alkyl group, or an alkyl group substituted by a member selected from the group consisting an alkoxy group, an amino group, an acylamino group, a sulfonyl amino group, an alkylthio group, a sulfonyl group, a sulfinyl group, a hydroxy group, a halogen atom, a sulfo group, a carboxyl group, and an acyloxy group, $L_{11}$ and $L_{12}$ represent an alkylene group respectively, W represents an alkylene group having 2 or more carbon atoms, and M represents a hydrogen atom or a cation.

2. A sulfonamide derivative according to claim 1, wherein the substituted alkyl group represented by R is substituted with a halogen atom.

3. A sulfonamide derivative according to claim 2, wherein said halogen atom is a fluorine atom.

4. A sulfonamide derivative according to claim 1, wherein the unsubstituted alkyl group represented by R is a methyl group.

5. A sulfonamide derivative according to claim 4, wherein the alkylene group represented by $L_{11}$ and $L_{12}$ is a methylene group or an ethylene group.

6. A sulfonamide derivative according to claim 1, wherein the alkylene group represented by W is an ethylene group or a propylene group.

7. A sulfonamide derivative according to claim 4, expressed by the formula:

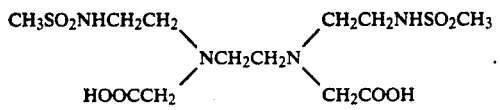

8. A sulfonamide derivative according to claim 1, expressed by the formula:

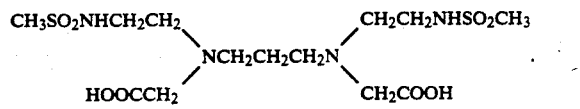

9. A sulfonamide derivative according to claim 1, expressed by the formula:

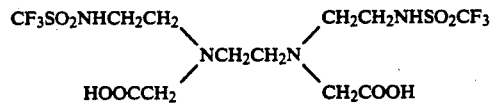

10. A sulfonamide derivative according to claim 1, expressed by the formula:

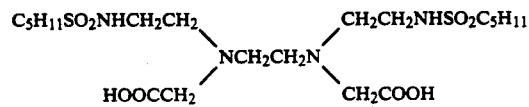

11. A sulfonamide derivative according to claim 1, expressed by the formula:

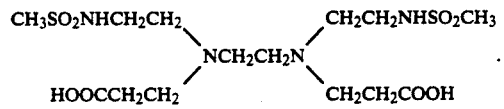

12. A sulfonamide derivative according to claim 1, expressed by the formula:

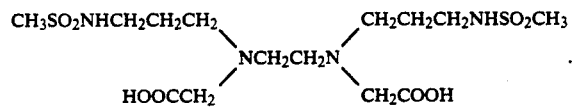

* * * * *